(12) United States Patent
Alexiou et al.

(10) Patent No.: US 9,655,946 B2
(45) Date of Patent: May 23, 2017

(54) DAPTOMYCIN FORMULATIONS AND USES THEREOF

(71) Applicant: HOSPIRA AUSTRALIA PTY LTD., Mulgrave North (AU)

(72) Inventors: Jim Alexiou, Oakleigh East (AU); Andrew Knill, Bittern (AU); Noel Norris, Endeavour Hills (AU); Darryl Whittaker, Vermont (AU)

(73) Assignee: HOSPIRA AUSTRALIA PTY LTD., Victoria (AU)

( * ) Notice: Subject to any disclaimer, the term of this patent is extended or adjusted under 35 U.S.C. 154(b) by 0 days.

(21) Appl. No.: 14/427,618

(22) PCT Filed: Sep. 11, 2013

(86) PCT No.: PCT/IB2013/002191
§ 371 (c)(1),
(2) Date: Mar. 11, 2015

(87) PCT Pub. No.: WO2014/041425
PCT Pub. Date: Mar. 20, 2014

(65) Prior Publication Data
US 2015/0313958 A1    Nov. 5, 2015

Related U.S. Application Data

(60) Provisional application No. 61/839,699, filed on Jun. 26, 2013, provisional application No. 61/699,570, filed on Sep. 11, 2012.

(51) Int. Cl.
| | |
|---|---|
| *A61K 38/12* | (2006.01) |
| *A61K 9/19* | (2006.01) |
| *A61K 47/12* | (2006.01) |
| *A61K 31/375* | (2006.01) |
| *A61K 38/16* | (2006.01) |
| *A61K 47/26* | (2006.01) |
| *A61K 31/404* | (2006.01) |
| *A61K 45/06* | (2006.01) |

(52) U.S. Cl.
CPC .............. *A61K 38/12* (2013.01); *A61K 9/19* (2013.01); *A61K 31/375* (2013.01); *A61K 31/404* (2013.01); *A61K 38/164* (2013.01); *A61K 45/06* (2013.01); *A61K 47/12* (2013.01); *A61K 47/26* (2013.01)

(58) Field of Classification Search
CPC ....................................................... A61K 9/19
See application file for complete search history.

(56) References Cited

U.S. PATENT DOCUMENTS

| | | | |
|---|---|---|---|
| 2002/0111311 A1 | 8/2002 | Govardhan et al. | |
| 2005/0209172 A1* | 9/2005 | Woo | A61K 9/0019 514/28 |
| 2007/0191280 A1 | 8/2007 | Kelleher et al. | |
| 2011/0124551 A1* | 5/2011 | Palepu | A61K 9/0019 514/2.9 |

FOREIGN PATENT DOCUMENTS

| | | |
|---|---|---|
| CN | 1616083 A | 5/2005 |
| WO | WO 2011/062676 A1 | 5/2011 |
| WO | WO 2011/063419 A2 | 5/2011 |
| WO | WO 2014/045296 A2 | 3/2014 |

OTHER PUBLICATIONS

Stoop et al., "Mannitol metabolism in plants: a method for coping with stress", Trends in Plant Science, 1996 pp. 139-144.*
Wu et al., "Antioxidant Activities of Carnosine, Anserine, Some Free Amino Acids and Their Combinations", Journal of Food and Drug Analysis, 2003, pp. 148-153.*
European Extended Search Report dated Nov. 3, 2015 in EP Application No. 13837694.2.
International Search Report mailed Dec. 23, 2013 in PCT/IB2013/002191.

* cited by examiner

*Primary Examiner* — Lianko Garyu
(74) *Attorney, Agent, or Firm* — Baker Botts L.L.P.

(57) ABSTRACT

Lyophilized daptomycin formulations having improved reconstitution times are provided. The lyophilized daptomycin formulations include an additive, which can be a pharmaceutically acceptable antioxidant, a pharmaceutically acceptable organic acid or a pharmaceutically acceptable salt thereof, a pharmaceutically acceptable glucose derivative or a pharmaceutically acceptable salt thereof, or a combination thereof. Also provided are methods of methods of preparing the lyophilized daptomycin formulations, and methods of treating bacterial infections and treating or preventing biofilms by using the lyophilized daptomycin formulations.

21 Claims, No Drawings

DAPTOMYCIN FORMULATIONS AND USES THEREOF

CROSS-REFERENCE TO RELATED APPLICATIONS

This application is a U.S. National Stage Patent Application under 35 U.S.C. §371 of International Application No. PCT/IB2013/002191, filed on Sep. 11, 2013, which claims priority under 35 U.S.C. §119 to U.S. Application Ser. No. 61/699,570, filed Sep. 11, 2012, and 61/839,699, filed Jun. 26, 2013, the disclosures of which are hereby incorporated by reference in their entireties, and to each of which priority is claimed.

FIELD

The presently disclosed subject matter relates to lyophilized daptomycin formulations having improved reconstitution times and methods of preparing thereof. The presently disclosed subject matter also relates to methods of treating a bacterial infection in a subject by using the lyophilized daptomycin formulations.

BACKGROUND

Daptomycin (I) is a cyclic lipopeptide derived from a natural product of *Streptomyces roseosporus*. The daptomycin comprises an asparagine (Asn) residue in the D configuration. Daptomycin has been used for treating complicated skin and skin structure infections (cSSSI) caused by susceptible isolates of the following gram-positive bacteria: *Staphylococcus aureus* (including methicillin-resistant isolates), *Streptococcus pyogenes*, *Streptococcus agalactiae*, *Streptococcus dysgalactiae* subsp. *equisimilis*, and *Enterococcus faecalis* (vancomycin-susceptible isolates only).

Daptomycin has also been used for treating *Staphylococcus aureus* bloodstream infections (bacteremia), including those with right-sided infective endocarditis, caused by methicillin-susceptible and methicillin-resistant isolates. Daptomycin's bactericidal effects stem from its ability to rapidly depolarize the membrane potential of gram-positive bacteria, which causes inhibition of DNA, RNA and protein synthesis, and results in cell death. The bactericidal effect of daptomycin is rapid, with greater than 99.9% of both MRSA and MSSA bacteria dead in less than one hour.

Daptomycin has also been used for biofilm treatment including catheter-related bloodstream infections (CRBSI) due to gram-positive bacteria. Particularly, daptomycin may be used for central venous catheter salvage for *S. aureus* and *S. epidermidis* infected catheters.

Daptomycin is commercially available as CUBICIN® ("the CUBICIN® product", Cubist Pharmaceuticals, Inc., Lexington, Mass.) and is supplied as a sterile, lyophilized powder. CUBICIN® is reconstituted in sodium chloride for parenteral injection. Stability studies have shown that the reconstituted solution is stable in a vial for 12 hours at room temperature and up to 48 hours if stored under refrigeration at 2 to 8° C. However, after this time, or at higher temperatures, daptomycin begins to degrade.

A major shortcoming of the commercially available daptomycin is that the reconstitution time of the CUBICIN® product is long and is typically in the range of about 15 to 45 minutes depending on the reconstitution procedure. This reconstitution time is not ideal in a therapeutic setting with respect to ease and efficiency of administration. Such long reconstitution time also increases the risk of inadvertent incomplete dissolution prior to administration and additionally increases the likelihood that the daptomycin will degrade prior to patient administration.

There are a number of daptomycin degradation products that have been identified. The major degradants of daptomycin are anhydro-daptomycin derivatives in which an α-aspartyl group is transpeptidated to an anhydrosuccinamido group, β-isomer of daptomycin in which the compound contains a β-aspartyl group instead of an α-aspartyl group and the lactone hydrolysis product of daptomycin in which one of the esters moieties is hydrolysed. The degradation pathway of daptomycin is described in U.S. Patent Publication No. 2007/191280.

High performance liquid chromatography (HPLC) of the reconstituted lyophilized powder can be used to determine the level of daptomycin relative to daptomycin degradants. Such comparison can thereby provide an indication of the stability of the daptomycin in the formulation. For example,

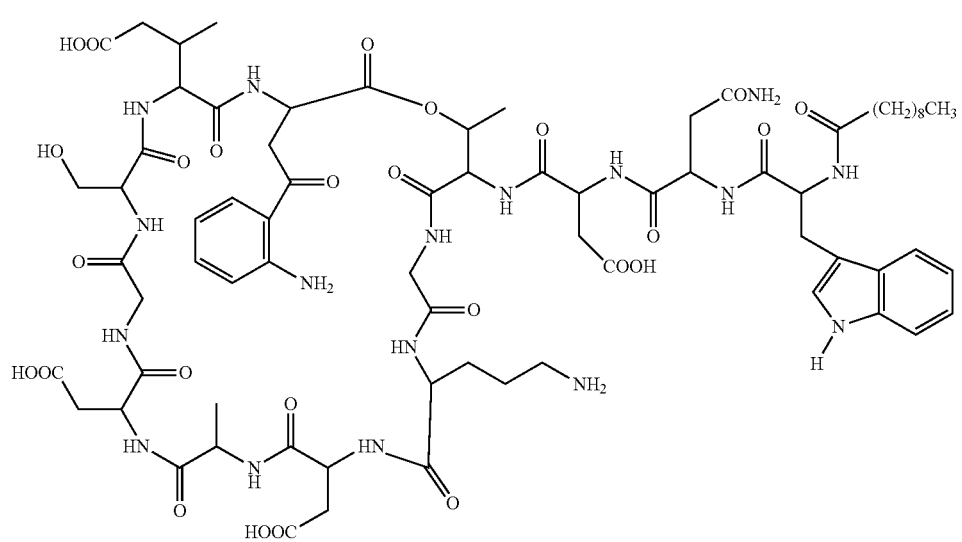

(I)

International Patent Publication No. WO2011/063419 discloses solid daptomycin preparations with improved reconstitution times and stability profiles relative to the CUBICIN® product. This is achieved when sugars, such as sucrose, and a phosphate buffer are introduced into the formulation. The formulations have a pH of about 6.5 to about 7.5. The sugars used can be non-reducing sugars and are included in the formulations in an amount of about 2.5% w/v to about 25% w/v. For example, the sugars are included in amounts of 15% w/v and 20% w/v.

There is still a need for alternative solid lyophilized daptomycin formulations that exhibit rapid reconstitution times, preferably in less than about 5 minutes, in a pharmaceutically accepted diluent. Additionally, there still remains need for solid daptomycin formulations that exhibit rapid reconstitution times and have improved stability in both solid and reconstituted forms. Such a solid formulation would be advantageous, as it would provide for a longer shelf life, a lessened requirement for refrigerated storage and a reduced handling time in reconstitution of the product before use. Such a formulation would also provide for more rapid administration and a more reliable dosing of daptomycin due to the presence of fewer impurities resulting from daptomycin degradation.

SUMMARY

The presently disclosed subject matter provides lyophilized daptomycin formulations having improved reconstitution times and methods of preparing thereof. Also provided are methods of treating a bacterial infection in a subject by using the lyophilized daptomycin formulations. The presently disclosed subject matter further provides methods of treating or preventing a biofilm by using the lyophilized daptomycin formulations.

The presently disclosed subject matter provides a lyophilized daptomycin formulation comprising an additive selected from the group consisting of pharmaceutically acceptable antioxidants, pharmaceutically acceptable organic acids and pharmaceutically acceptable salts thereof, pharmaceutically acceptable glucose derivatives and pharmaceutically acceptable salts thereof, and combinations thereof. In certain embodiments, the lyophilized daptomycin formulation includes from about 200 mg to about 600 mg of daptomycin. In certain embodiments, the lyophilized daptomycin formulation includes from about 0.01 mM to about 500 mM of the additive.

In one embodiment, the pharmaceutically acceptable antioxidant is ascorbic acid. The pharmaceutically acceptable organic acid can be selected from the group consisting of monocarboxylic organic acids, dicarboxylic organic acids, hydroxyl substituted dicarboxylic organic acids, tricarboxylic organic acids, hydroxyl substituted tricarboxylic organic acids, tetracarboxylic organic acids, and combinations thereof. In certain embodiments, the pharmaceutically acceptable organic acid is a hydroxyl substituted tricarboxylic organic acid. In one embodiment, the hydroxyl substituted tricarboxylic organic acid is citric acid. In one embodiment, the pharmaceutically acceptable glucose derivative is acetyl glucosamine.

The lyophilized daptomycin formulation can be reconstituted in a pharmaceutically acceptable diluent. In one embodiment, the lyophilized daptomycin formulation is reconstituted in a pharmaceutically acceptable diluent in less than about 5 minutes. The concentration of daptomycin in the reconstituted lyophilized daptomycin formulation can be from about 20 mg/mL to about 100 mg/mL.

The concentration of the additive in the reconstituted lyophilized daptomycin formulation can be from about 1 mM to about 500 mM. In one embodiment, the concentration of the additive in the reconstituted lyophilized daptomycin formulation is about 237.5 mM. In one embodiment, the concentration of the additive in the reconstituted lyophilized daptomycin formulation is about 300 mM. In certain embodiments, the concentration of the additive in the reconstituted lyophilized daptomycin formulation is from about 1 mg/mL to about 500 mg/mL.

The pH of the reconstituted lyophilized daptomycin formulation can be from about 4.0 to about 5.0. In one embodiment, the pH of the reconstituted lyophilized daptomycin formulation is about 4.7.

The diluent can be selected from the group consisting of sterile water for injection, bacteriostatic water for injection, 0.45% sodium chloride solution for injection, 0.9% sodium chloride solution for injection, Ringer's solution, lactated Ringer's solution, and combinations thereof. In one embodiment, the diluent is 0.9% sterile sodium chloride solution for injection. In another embodiment, the diluent is sterile water for injection.

The presently disclosed subject matter also provides a method of treating a bacterial infection in a subject. The method includes administering to a subject in need thereof, an effective amount of the above-disclosed lyophilized daptomycin formulation. Additionally, the presently disclosed subject matter provides a method of treating or preventing a biofilm. The method includes exposing a surface of a device to a solution of an effective amount of the above-disclosed lyophilized daptomycin formulation.

The presently disclosed subject matter further provides methods for preparing lyophilized daptomycin formulations. In one embodiment, the method includes (a) forming an aqueous solution of daptomycin and an additive, which is selected from the group consisting of pharmaceutically acceptable organic acids and pharmaceutically acceptable salts thereof, pharmaceutically acceptable glucose derivatives and pharmaceutically acceptable salts thereof, and combinations thereof; (b) adjusting the pH to about 4.0 to about 5.0; and (c) lyophilising the solution to obtain a lyophilisate. In another embodiment, the method includes (a) forming an aqueous solution of daptomycin at a pH of about 4.0 to about 5.0; (b) dissolving an additive selected from the group consisting of pharmaceutically acceptable organic acids and pharmaceutically acceptable salts thereof, pharmaceutically acceptable glucose derivatives and pharmaceutically acceptable salts thereof, and combinations thereof in the aqueous solution of the daptomycin; (c) adjusting the pH to about 4.0 to about 5.0; and (d) lyophilising the solution to obtain a powder.

DETAILED DESCRIPTION

Definitions

The examples provided in the definitions present in the present application are non-inclusive unless otherwise stated. They include but are not limited to the recited examples.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "osmolality" of a solution means the number of osmoles of solute per kilogram of solvent. Osmolality is a measure of the osmotic pressure exerted by a real solution across a semi-permeable membrane. It can be measured by use of a property of the solution that is dependent only on the particle concentration. These properties include vapour pressure depression, freezing point and boiling point depression, osmotic pressure collectively referred to as colligative properties. The osmolality of a solution is typically determined most accurately and conveniently by measuring freezing point depression.

As used herein, the term "lyophilized" means a stabilizing process used to remove a solvent from tissue, blood, serum, pharmaceutical formulations, or other biological substances; at low temperatures through a process of sublimation (primary drying) and then desorption (secondary drying). A lyophilized formulation can be reconstituted in a simple manner to give a ready-to-use solution which contains no visible particles by addition of a diluent.

Lyophilized Daptomycin Formulations

The presently disclosed subject matter provides a lyophilized daptomycin formulation including an additive. The additive can be a pharmaceutically acceptable antioxidant, a pharmaceutically acceptable organic acid and a pharmaceutically acceptable salt thereof, a pharmaceutically acceptable glucose derivative and a pharmaceutically acceptable salt thereof, and a combination thereof.

The lyophilized daptomycin formulation of the presently disclosed subject matter displays rapid reconstitution times in a pharmaceutically acceptable diluent. Furthermore, the inclusion of an additive in the daptomycin formulations does not adversely affect the stability of the formulations with respect to the CUBICIN® product. The lyophilized daptomycin formulations of the presently disclosed subject matter display good pharmaceutical elegance and upon reconstitution display minimal foaming. The presence of foaming upon reconstitution can be problematic with daptomycin solutions due to its amphiphilic properties, particularly in a clinical setting wherein foaming of the formulation affects the reconstitution time, the homogeneity of the reconstituted solution, as well as the ease and accuracy of delivering the formulation to a patient. The lyophilized daptomycin formulations of the presently disclosed subject matter thereby allow for simple and rapid reconstitution and provide daptomycin solution formulations with improved homogeneity that can be more easily and precisely delivered to a patient.

Additives

The additives suitable for use in the formulations of the presently disclosed subject matter can be pharmaceutically acceptable antioxidants, pharmaceutically acceptable organic acids or salts thereof, pharmaceutically acceptable antioxidants, pharmaceutically acceptable glucose derivatives or salts thereof, or combinations thereof.

The additives suitable for use in the formulations of the presently disclosed subject matter can be pharmaceutically acceptable antioxidants. Suitable antioxidants include, but are not limited to, ascorbic acid, monothioglycerol, L-cysteine, thioglycolic acid, sodium metabisulfite, sodium EDTA, monoethanolamine gentisate, sodium formaldehyde sulfoxylate and sodium bisulfite. In one embodiment, the antioxidant is ascorbic acid.

The organic acids suitable for use in the presently disclosed subject matter include, but are not limited to, monocarboxylic organic acids, dicarboxylic organic acids, hydroxyl substituted dicarboxylic organic acids, tricarboxylic organic acids, and tetracarboxylic organic acids.

In one embodiment, the dicarboxylic organic acid is a hydroxyl substituted dicarboxylic organic acid. In another embodiment, the tricarboxylic organic acid is a hydroxyl substituted tricarboxylic organic acid.

Monocarboxylic organic acids suitable for use in the presently disclosed subject matter include, but are not limited to, acetic acid, lactic acid, thiolactic acid, glycolic acid, butyric acid, isobutyric acid, glyceric acid, oxaloacetic acid, pyruvic acid, propionic acid, valeric acid, pivalic acid and benzoic acid. In one embodiment, the monocarboxylic acid is acetic acid. In another embodiment, the pharmaceutically acceptable salt of a monocarboxylic organic acid is sodium acetate. In yet another embodiment, the pharmaceutically acceptable salt of a monocarboxylic organic acid is potassium acetate.

Dicarboxylic organic acids suitable for use in the presently disclosed subject matter include, but are not limited to, malonic acid, succinic acid, adipic acid, maleic acid and glutaric acid. In one embodiment, the dicarboxylic organic acid is succinic acid.

Hydroxyl substituted dicarboxylic organic acids suitable for use in the presently disclosed subject matter include, but are not limited to, glucaric acid, α-hydroxyglutaric acid, gluconic acid, malic acid and tartaric acid. In one embodiment, the hydroxyl substituted dicarboxylic organic acid is tartaric acid.

Tricarboxylic organic acids suitable for use in the presently disclosed subject matter include, but are not limited to, aconitic acid and oxalosuccinic acid.

Hydroxyl substituted tricarboxylic organic acids suitable for use in the presently disclosed subject matter include, but are not limited to, citric acid, isocitric acid, homocitric acid and hydroxycitric acid. In one embodiment, the hydroxyl substituted tricarboxylic organic acid is citric acid.

Tetracarboxylic organic acids suitable for use in the presently disclosed subject matter include, but are not limited to, edetic acid, ethylene tetracarboxylic acid and ethylene glycol tetraacetic acid. The suitable pharmaceutically acceptable salts of tetracarboxylic organic acids include, but are not limited to, disodium edetate and tetrasodium edetate. In one embodiment, the tetracarboxylic organic acid is edetic acid. In another embodiment, the pharmaceutically acceptable salt of a tetracarboxylic organic acid is disodium edetate.

Furthermore, the additives suitable for use in the formulations of the presently disclosed subject matter can be pharmaceutically acceptable glucose derivatives or salts thereof. In one embodiment, the glucose derivative is acetyl glucosamine.

When the additive is a pharmaceutically acceptable salt of a pharmaceutically acceptable organic acid or a pharmaceutically acceptable glucose derivative, the salt may be formed in situ by the addition of a pharmaceutically acceptable base to an acid solution. Alternatively, the salt may be added directly to the formulation. The cation of the salt includes, but is not limited to, sodium, potassium, lithium, calcium, magnesium, zinc, ammonium, alkylammonium (such as triethylammonium), alkoxyammonium (such as ethanolammonium and ethanediaminium), choline and amino acids (such as arginine, lysine or histidine).

The lyophilized daptomycin formulations of the presently disclosed subject matter can include 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475 and 500 mM, or a range including any of two of those integers, of an additive.

In some embodiments, the lyophilized daptomycin formulation includes from about 0.01 mM to about 500 mM of an additive. The lyophilized daptomycin formulation can include from about 0.05 mM to about 450 mM, from about 0.05 mM to about 300 mM, or from about 0.05 mM to about 100 mM, of an additive.

In one embodiment, the additive is a combination of a pharmaceutically acceptable antioxidant, a pharmaceutically acceptable organic acid, a pharmaceutically acceptable salt thereof, a pharmaceutically acceptable glucose derivative, and/or a pharmaceutically acceptable salt thereof. The concentration of the additive is the sum of the concentrations of the antioxidant, the organic acid, the salt thereof, the glucose derivative, and/or the salt thereof expressed in terms of minimolar (mM) or mass per volume (mg/mL). In one embodiment, the salt is the conjugate base of the organic acid so as to form a buffer solution.

In certain embodiments, the additive is used at a concentration that does not destabilise the daptomycin and preferably aids stability of the daptomycin. The stability of daptomycin will depend on the intended shelf life of the pharmaceutical formulation and the manipulation prior to administration. In one embodiment, the daptomycin formulations of the presently disclosed subject matter are at least as stable as the CUBICIN®) lyophilized powder.

Daptomycin

The CUBICIN® product includes 250, 350 or 500 mg of daptomycin. The lyophilized daptomycin formulations of the presently disclosed subject matter include from about 200 mg to about 600 mg of daptomycin. In some embodiments, the lyophilized daptomycin formulations include from about 200 mg to about 300 mg of daptomycin. In one embodiment, the lyophilized daptomycin formulations include about 250 mg of daptomycin. In some embodiments, the lyophilized daptomycin formulations include from about 300 mg to about 400 mg of daptomycin. In one embodiment, the lyophilized daptomycin formulations include about 350 mg of daptomycin. In certain embodiments, the lyophilized daptomycin formulations include from about 450 mg to about 550 mg of daptomycin. In one embodiment, the lyophilized daptomycin formulations include about 500 mg of daptomycin.

Optional Components

Further optional components can be included in the lyophilized daptomycin formulations. Such optional components include, but are not limited to, buffering agents, stabilisers, solubilisers, crystallisation inhibitors, surfactants and tonicifying agents.

The lyophilized daptomycin formulations of the presently disclosed subject matter can optionally include one or more buffering agents. Suitable buffering agents include, but are not limited to, phosphate buffers, sulfonic acids and Tris buffers. Specific buffers include sodium or potassium salts of phosphoric acid (such as disodium hydrogen phosphate), 2-(N-morpholino)ethanesulfonic acid (MES), N-[tris(hydroxymethyl)methyl]-2-aminoethanesulfonic acid (TES), N-(2-hydroxyethyl)piperazine-N'-(2-ethanesulfonic acid) (HEPES), 3-(N,N-Bis[2-hydroxyethl]amino)-2-hydroxypropanesulfonic acid (DIPSO), 2-hydroxy-3-[trishydroxymethyl)methylamine]-1-propanesulfonic acid (TAPSO), N-(2-acetamido)2-aminoethanesulfonic acid (ACES), 1,4-piperazinediethanesulfonic acid (PIPES), 3-(N-morpholino) propanesulfonic acid (MOPS), β-hydroxy-4-morpholinepropanesulfonic acid (MOPSO), N-(2-acetamido)-iminodiacetic acid (ADA) and 2-bis(2-hydroxyethyl)amino-2-(hydroxymethyl)-1,3-propanediol (BIS-TRIS). The buffering agent can be added in an amount of about 0.01 mM to about 500 mM to the lyophilized daptomycin formulations.

The lyophilized daptomycin formulations of the presently disclosed subject matter can optionally include one or more stabilisers. Suitable stabilising agents include, but are not limited to, sugars (such as sucrose, trehalose and dextran), amino acids (such as arginine, glycine and histidine), polyvinylpyrrolidones (povidone) and polyols (such as mannitol and polymeric polyol surfactants, e.g., Pluronic®.

Reconstitution of Lyophilized Daptomycin Formulations

The lyophilized daptomycin formulations of the presently disclosed subject matter display rapid reconstitution times in a pharmaceutically acceptable diluent. In one embodiment, the lyophilized daptomycin formulations are reconstituted in a pharmaceutically acceptable diluent in less than about 5 minutes. In one embodiment, the lyophilized daptomycin formulations are reconstituted in a pharmaceutically acceptable diluent in less than about 4 minutes. In one embodiment, the lyophilized daptomycin formulations are reconstituted in a pharmaceutically acceptable diluent in less than about 3 minutes. In another embodiment, the lyophilized daptomycin formulations are reconstituted in a pharmaceutically acceptable diluent in less than about 2 minutes. In yet another embodiment, the lyophilized daptomycin formulations are reconstituted in a pharmaceutically acceptable diluent in less than about 1 minute. The lyophilized daptomycin formulations of the presently disclosed subject matter have improved reconstitution times compared to the CUBICIN® product.

The CUBICIN® product is reconstituted in 0.9% sterile sodium chloride for injection. The lyophilized daptomycin formulations of the presently disclosed subject matter can be reconstituted with one or more pharmaceutically acceptable diluents to provide a solution suitable for administration. Pharmaceutically acceptable diluents of the presently disclosed subject matter include, but are not limited to, sterile water for injection, bacteriostatic water for injection, 0.45% sodium chloride solution for injection and 0.9% sodium chloride solution for injection, Ringer's solution and lactated Ringer's solution. In one embodiment, the lyophilized daptomycin formulations are reconstituted in 0.9% sterile sodium chloride solution for injection. In another embodiment, the lyophilized daptomycin formulations are reconstituted in sterile water for injection.

The lyophilized daptomycin formulations of the presently disclosed subject matter can be reconstituted by adding the pharmaceutically acceptable diluent(s) to the lyophilized daptomycin formulation to provide the desired concentration for direct administration or further dilution for administration by infusion. In some embodiments, the volume of the pharmaceutically acceptable diluent(s) added to the lyophilized daptomycin formulation is from about 5 mL to about 15 mL. In some embodiments, the volume of the pharmaceutically acceptable diluent(s) added to the lyophilized daptomycin formulation is from about 8 mL to about 12 mL. In one embodiment, the volume of the pharmaceutically acceptable diluent(s) added to the lyophilized daptomycin formulation is about 10 mL.

The lyophilized daptomycin formulations of the presently disclosed subject matter can be reconstituted by any suitable methods known to one of ordinary skill in the art. In one embodiment, 10 mL of 0.9% sterile sodium chloride for injection is added slowly to a vial including 500 mg of the lyophilized daptomycin formulation of the presently disclosed subject matter. The resultant mixture is rotated to ensure all of the formulation is wetted and then allowed to stand undisturbed for about 2 minutes. The vial is then gently rotated or swirled intermittently as needed, to obtain a completely reconstituted solution. Additionally and alternatively, the reconstitution method includes quickly adding a diluent to a vessel including a lyophilized daptomycin formulation of the presently disclosed subject matter, followed by swirling of the vessel if required. In some embodiments, the diluent is added in a period of 1-60 seconds. In some embodiments, the diluent is added in a period of about 1-30 seconds. In one embodiment, the diluent is added in less than about 20 seconds. In one embodiment, after adding the diluent to the presently disclosed daptomycin formulation, the vessel including the daptomycin is swirled for about 1 minute and allowed to stand for about 3-5 minutes until clear.

Upon reconstitution in a pharmaceutically acceptable diluent, the CUBICIN® product includes 50 mg/mL daptomycin. Upon reconstitution in a pharmaceutically acceptable diluent, when provided in a vial, the daptomycin formulations of the presently disclosed subject matter include daptomycin at a concentration of from about 20 mg/mL to about 100 mg/mL, e.g., from about 20 mg/mL to about 30 mg/mL, from about 30 mg/mL to about 40 mg/mL, from about 40 mg/mL to about 50 mg/mL, from about 50 mg/mL to about 60 mg/mL, from about 60 mg/mL to about 70 mg/mL, from about 70 mg/mL to about 80 mg/mL, from about 80 mg/mL to about 90 mg/mL, or from about 90 mg/mL to about 100 mg/mL. In one embodiment, upon reconstitution in a pharmaceutically acceptable diluent, when provided in a vial, the daptomycin formulations include daptomycin at a concentration of about 50 mg/mL. In another embodiment, upon reconstitution in a pharmaceutically acceptable diluent, when provided in a vial, the daptomycin formulations include daptomycin at a concentration of about 62.5 mg/mL.

The reconstituted daptomycin formulation can be further diluted in a pharmaceutically acceptable diluent for administration to a subject. Pharmaceutically acceptable diluents include, but are not limited to, sterile water for injection, bacteriostatic water for injection, 0.45% sodium chloride solution for injection, 0.9% sodium chloride solution for injection, Ringer's solution and lactated Ringer's solution. In one embodiment, when the reconstituted daptomycin formulation is further diluted for administration to a subject, the final daptomycin concentration is from about 2.5 to about 20 mg/mL.

Upon reconstitution in a pharmaceutically acceptable diluent, the daptomycin formulations of the presently disclosed subject matter include an additive at a concentration of 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475 and 500 mM, or a range including any of two of those integers. In some embodiments, upon reconstitution in a pharmaceutically acceptable diluent, the presently disclosed daptomycin formulations include an additive at a concentration of from about 1 mM to about 500 mM, from 1 mM to about 250 mM, or from about 1 mM to about 150 mM. For example, the concentration of the additive in the reconstituted daptomycin formulations can be from 1 mM to about 50 mM, from about 50 mM to about 100 mM (e.g., from about 80 mM to about 120 mM), from about 100 mM to about 150 mM, from about 150 mM to about 200 mM, from about 200 mM to about 250 mM (e.g., from about 200 mM to about 240 mM, from about 220 mM to about 240 mM, from about 230 mM to about 240 mM, or from about 240 mM to about 250 mM), from about 250 mM to about 350 mM (e.g., from about 250 mM to about 340 mM, from about 260 mM to about 330 mM, from about 270 mM to about 320 mM, from about 280 mM to about 310 mM, from about 290 mM to about 300 mM, or from about 340 mM to about 350 mM), or from about 350 mM to about 400 mM, from about 400 mM to about 450 mM, or from about 450 mM to about 500 mM. In certain embodiments, the concentration of the additive in the reconstituted lyophilized daptomycin formulation is about 237.5 mM. In certain embodiments, the concentration of the additive in the reconstituted lyophilized daptomycin formulation is about 300 mM. In some embodiments, the concentration of the additive in the reconstituted lyophilized daptomycin formulation is about 500 mM.

In one embodiment, the additive is ascorbic acid. The concentration of ascorbic acid in the reconstituted lyophilized daptomycin formulation is about 237.5 mM. Additionally or alternatively, the concentration of ascorbic acid in the reconstituted lyophilized daptomycin formulation is about 300 mM.

In one embodiment, the additive is succinic acid. The concentration of succinic acid in the reconstituted formulation is from about 1 mM to about 500 mM, from about 1 mM to about 250 mM, or from about 80 mM to about 120 mM.

In one embodiment, the additive is tartaric acid. The concentration of tartaric acid in the reconstituted formulation is from about 1 mM to about 500 mM, from about 1 mM to about 250 mM, or from about 80 mM to about 120 mM.

In one embodiment, the additive is citric acid. The concentration of citric acid in the reconstituted formulation is from about 1 mM to about 500 mM, from about 1 mM to about 250 mM, or from about 25 mM to about 75 mM. In one embodiment, the concentration of citric acid in the reconstituted formulation is about 237.5 mM. Additionally or alternatively, the concentration of citric acid in the reconstituted formulation is about 300 mM. The concentration of citric acid in the reconstituted formulation can also be about 500 mM.

In one embodiment, the additive is edetic acid. The concentration of edetic acid in the reconstituted formulation is from about 1 to about 500 mM, from about 1 to about 250 mM, or from about 50 mM to about 100 mM.

In another embodiment, the additive is acetyl glucosamine. The concentration of acetyl glucosamine in the reconstituted lyophilized daptomycin formulation is about 237.5 mM. Additionally or alternatively, the concentration of acetyl glucosamine in the reconstituted lyophilized daptomycin formulation is about 300 mM.

In certain embodiments, upon reconstitution in a pharmaceutically acceptable diluent, the presently disclosed daptomycin formulations include an additive at a concentration of 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475 and 500 mg/mL, or a range including any of two of those integers. In one embodiment, upon reconstitution in a pharmaceutically acceptable diluent, the presently disclosed daptomycin formulations include an additive at a concentration of from about 1 mg/mL to about 500 mg/mL, from about 1 mg/mL to about 250 mg/mL, or from about 1 mg/mL to about 100 mg/mL. For example, the concentration of the additive in the reconstituted daptomycin formulations can be from about 1 mg/mL to about 50 mg/mL (e.g., from about 10 mg/mL to about 50 mg/mL, from about 20 mg/mL to about 50 mg/mL, from about 30 mg/mL to about 50 mg/mL, or from about 40 mg/mL to about 50 mg/mL), from about 50 mg/mL to about 100 mg/mL (e.g., from about 50 mg/mL to about 90 mg/mL, from about 50 mg/mL to about 80 mg/mL, from about 50 mg/mL to about 70 mg/mL, from about 50 mg/mL to about 60 mg/mL, from about 60 mg/mL to about 70 mg/mL, or from about 90 mg/mL to about 100 mg/mL), from about 100 mg/mL to about 150 mg/mL, from about 150 mg/mL to about 200 mg/mL, from about 200 mg/mL to about 250 mg/mL, from about 250 mg/mL to about 300 mg/mL, from about 300 mg/mL to about 350 mg/mL, from about 350 mg/mL to about 400 mg/mL, from about 400 mg/mL to about 450 mg/mL, or from 450 mg/mL to about 500 mg/mL.

In one embodiment, the additive is ascorbic acid. The concentration of ascorbic acid in the reconstituted lyophilized daptomycin formulation is about 41.8 mg/mL. Additionally or alternatively, the concentration of ascorbic acid in the reconstituted lyophilized daptomycin formulation is about 52.8 mg/mL.

In one embodiment, the additive is succinic acid. The concentration of succinic acid in the reconstituted formulation is from about 1 mg/mL to about 500 mg/mL, from about 1 mg/mL to about 250 mg/mL, or from about 1 mg/mL to about 50 mg/mL.

In one embodiment, the additive is tartaric acid. The concentration of tartaric acid in the reconstituted formulation is from about 1 mg/mL to about 500 mg/mL, from about 1 mg/mL to about 250 mg/mL, or from about 1 mg/mL to about 50 mg/mL.

In one embodiment, the additive is citric acid. The concentration of citric acid in the reconstituted formulation can be from about 1 mg/mL to about 500 mg/mL, from about 1 mg/mL to about 250 mg/mL, or from about 1 mg/mL to about 50 mg/mL. In one embodiment, the concentration of citric acid in the reconstituted lyophilized daptomycin formulation is about 45.6 mg/mL. Additionally or alternatively, the concentration of citric acid in the reconstituted lyophilized daptomycin formulation is about 57.6 mg/mL. The concentration of citric acid in the reconstituted lyophilized daptomycin formulation can also be about 96.1 mg/mL.

In one embodiment, the additive is edetic acid. The concentration of edetic acid in the reconstituted formulation is from about 1 mg/mL to about 500 mg/mL, from about 1 mg/mL to about 250 mg/mL, or from about 1 mg/mL to about 50 mg/mL.

In another embodiment, the additive is acetyl glucosamine. The concentration of acetyl glucosamine in the reconstituted lyophilized daptomycin formulation is about 52.5 mg/mL. Additionally or alternatively, the concentration of acetyl glucosamine in the reconstituted lyophilized daptomycin formulation is about 66.4 mg/mL.

In certain embodiments, upon reconstitution in a pharmaceutically acceptable diluent, the pH of the presently disclosed daptomycin formulations is in the range of from about 4.0 to about 7.0. In one embodiment, the pH is in the range of from about 4.0 to about 5.0.

The purity of the daptomycin in the lyophilized daptomycin formulations of the presently disclosed subject matter can be measured by any means known to one of ordinary skill in the art, including nuclear magnetic resonance (NMR), or high performance liquid chromoatography coupled with UV (HPLC/UV) or mass spectrometry (HPLC/MS). In one embodiment, the purity of the lyophilized daptomycin formulations is measured by reconstitution in a pharmaceutically acceptable diluent followed by analysis employing HPLC/UV. The HPLC/UV process utilised for measuring the purity of the lyophilized daptomycin formulations can be any method known to one of ordinary skill in the art, e.g., using appropriate HPLC/UV machines typically encountered in the industry, such as the HPLC/UV process described in US Patent 2007/191280 A1. In one non-limiting example, the purity of daptomycin in a reconstituted solution of a lyophilized daptomycin formulation of the presently disclosed subject matter can be determined by HPLC/UV followed by analysis of the peak area (the area-under-the curve-(AUC)) at a wavelength of 223 nm for individual peaks of the chromatogram. The amount of daptomycin can be measured with respect to the total amount of impurities present. Further, the relative amount of daptomycin with respect to three of the known daptomycin degradants, specifically the anhydro-daptomycin, the β-isomer of daptomycin and the lactone hydrolysis product of daptomycin can be determined.

In one embodiment, the lyophilized daptomycin formulations of the presently disclosed subject matter include daptomycin in a purity that is higher than that of CUBICIN® product as determined by HPLC/UV analysis of the reconstituted solution at a wavelength of 223 nm. In another embodiment, the lyophilized daptomycin formulations of the presently disclosed subject matter include total impurities in an amount of less than that of the CUBICIN® product as determined by HPLC/UV analysis of the reconstituted solution at a wavelength of 223 nm.

Methods of Using Lyophilized Daptomycin Formulations

The presently disclosed subject matter further provides a method of treating a bacterial infection in a subject. The method includes administering to a subject in need thereof, an effective amount of a lyophilized daptomycin formulation including an additive selected from the group consisting of pharmaceutically acceptable antioxidants, pharmaceutically acceptable organic acids and pharmaceutically acceptable salts thereof, pharmaceutically acceptable glucose derivatives and a pharmaceutically acceptable salts thereof, and combinations thereof.

The presently disclosed subject matter further provides a method of treating or preventing a biofilm. The method includes exposing a surface of a device to a solution of an effective amount of a lyophilized daptomycin formulation including an additive selected from the group consisting of pharmaceutically acceptable antioxidants, pharmaceutically acceptable organic acids and pharmaceutically acceptable salts thereof, pharmaceutically acceptable glucose derivatives and a pharmaceutically acceptable salts thereof, and combinations thereof.

Methods of Preparing Lyophilized Daptomycin Formulations

Furthermore, the presently disclosed subject matter provides a method for preparing the presently disclosed lyophilized daptomycin formulation. The lyophilized daptomycin formulation can be lyophilized from any solvent known to be suitable in the art. Acceptable solvents include, but are not limited to, water, aqueous butanol and aqueous ethanol. The lyophilisation process utilised to prepare the presently disclosed lyophilized daptomycin formulations can be any method known to one of ordinary skill in the art using appropriate freeze drying machines typically encountered in the industry. Exemplary lyophilisation processes include those described in "Lyophilization: Introduction and Basic Principles" by Thomas A Jennings, InterPharm Press, 1999. In some embodiments, the method includes: (a) forming an aqueous solution of the daptomycin and the additive selected from the group consisting of pharmaceutically acceptable antioxidants, pharmaceutically acceptable organic acids and pharmaceutically acceptable salts thereof, pharmaceutically acceptable glucose derivatives and a pharmaceutically acceptable salts thereof, and combinations thereof, (b) adjusting the pH to about 4.0 to about 5.0; and (c) lyophilising the solution to obtain a lyophilisate. In one embodiment, the method includes: (a) forming an aqueous solution of the daptomycin at a pH of about 4.0 to about 5.0; (b) dissolving the additive selected from the group consisting of pharmaceutically acceptable antioxidants, pharmaceutically acceptable organic acids and pharmaceutically acceptable salts thereof, pharmaceutically acceptable glucose derivatives and a pharmaceutically acceptable salts thereof, and combinations thereof in the aqueous solution of the daptomycin; (c) adjusting the pH to about 4.0 to about 5.0; and (d) lyophilising the solution to obtain a powder. In another embodiment, the method includes: (a) forming an aqueous tertiary-butanol solution of the daptomycin at a pH of 4.0 to 5.0; (b) dissolving an additive selected from the group consisting of pharmaceutically acceptable antioxidants, pharmaceutically acceptable organic acids and pharmaceutically acceptable salts thereof, pharmaceutically acceptable glucose derivatives and a pharmaceutically acceptable salts thereof, and combinations thereof in the aqueous/butanol solution of the daptomycin; (c) adjusting the pH to about 4.0 to about 5.0; and (d) lyophilising the solution to obtain a powder.

EXAMPLES

The following examples are merely illustrative of the presently disclosed subject matter and they should not be considered as limiting the scope of the invention in any way.

Example 1

I. Lyophilized Daptomycin Formulations

Table 1 provides examples of daptomycin formulation solutions that were subsequently lyophilized to produce lyophilized formulations of the presently disclosed subject matter including an additive selected from the group consisting of pharmaceutically acceptable antioxidants, pharmaceutically acceptable organic acids and pharmaceutically acceptable salts thereof, pharmaceutically acceptable glucose derivatives and pharmaceutically acceptable salts thereof, and combinations thereof.

TABLE 1

| Formulation | Formulation Components |
| --- | --- |
| A | Daptomycin (350 mg/vial), Citric acid (56 mg/vial) NaOH (2M, 0.14 mL/vial) Water Additional NaOH to adjust pH |
| B | Daptomycin (350 mg/vial) Tartaric acid (84 mg/vial), NaOH (2M, 0.14 mL/vial) Water Additional NaOH to adjust pH |
| C | Daptomycin (350 mg/vial), Succinic acid (67.2 mg/vial), NaOH (2M, 0.14 mL/vial) Water Additional NaOH to adjust pH |
| D | Daptomycin (350 mg/vial), Edetic acid (140 mg/vial), NaOH (2M, 0.14 mL/vial) Water Additional NaOH to adjust pH |
| E | Daptomycin (350 mg/vial), NaOH (2M, 0.14 mL/vial) ʹButanol (1.12 mL/vial) Water Additional NaOH to adjust pH |
| F | Daptomycin (350 mg/vial), Citric acid (56 mg/vial), Water |

II. Analysis of Daptomycin Formulations

Reconstitution time was determined by injecting 7 mL of 0.9% sterile sodium chloride for injection to a vial including 350 mg of the lyophilized daptomycin formulation. The resultant mixture was swirled for about 1 minute and allowed to stand. The reconstitution time is the time required from addition of the diluent to total dissolution of the daptomycin formulation.

Table 2 provides reconstitution times of the lyophilized daptomycin formulations including an additive in 0.9% sterile sodium chloride for injection. Initial reconstitution times, and reconstitution after 1, 3 or 6 months of storage at 5° C., 25° C. and 40° C. for the compositions are provided. The pH of the reconstituted lyophilized daptomycin formulations is 4.7. The reconstitution times of the CUBICIN® product are included for comparison.

TABLE 2

|  | Initial | 3 months | 6 months |
|---|---|---|---|
| Formulation at 5° C. | | | |
| A | 2 min 40 sec | 1 min 35 sec | Not tested |
| B | 1 min 10 sec | 2 min 0 sec | Not tested |
| C | 3 min 20 sec | 5 min 50 sec | Not tested |
| D | 2 min 30 sec | 2 min 10 sec | Not tested |
| E | Not tested | Not tested | Not tested |
| CUBICIN ® | 18 min 00 sec | 21 min 30 sec | 13 min 00 sec |
| Formulation at 25° C. | | | |
| A | 2 min 40 sec | 2 min 35 sec | 2 min 45 sec |
| B | 1 min 10 sec | 1 min 0 sec | Not tested |
| C | 3 min 20 sec | 4 min 40 sec | Not tested |
| D | 2 min 30 sec | 1 min 0 sec | Not tested |
| E | 10 min 30 sec | Not tested | Not tested |
| CUBICIN ® | 18 min 00 sec | 14 min 55 sec | 14 min 42 sec |
| Formulation at 40° C. | | | |
| A | 2 min 40 sec | 1 min 50 sec | Not tested |
| B | Not tested | Not tested | 0 min 55 sec |
| C | 1 min 10 sec | 1 min 0 sec | Not tested |
| D | 3 min 20 sec | 11 min 30 sec | Not tested |
| E | 2 min 30 sec | 1 min 0 sec | Not tested |
| F | Not tested | Not tested | Not tested |
| CUBICIN ® | 18 min 00 sec | Not tested | Not tested |

The effect of pH on the reconstitution time of the daptomycin lyophilized powder including citric acid was assessed. Table 3 provides the reconstitution times in 0.9% sterile sodium chloride for injection of lyophilized daptomycin formulations including 350 mg daptomycin, 56 mg citric acid and sodium hydroxide sufficient to adjust the pH of the lyophilisation solution upon reconstitution of the lyophilized formulation. Initial reconstitution times and reconstitution times after 3 months of storage at 40° C. for the compositions is provided.

TABLE 3

| Formulation pH | Initial | 3 months |
|---|---|---|
| 2.5 | 3 min 0 sec | 2 min 30 sec |
| 3.0 | 3 min 0 sec | 2 min 30 sec |
| 3.3 | >5 min 0 sec | 3 min 15 sec |
| 3.5 | >5 min 0 sec | 4 min 30 sec |
| 3.8 | >5 min 0 sec | 4 min 54 sec |
| 4.0 | 1 min 50 sec | 5 min 00 sec |
| 4.3 | 1 min 30 sec | 2 min 20 sec |
| 4.5 | 1 min 20 sec | 3 min 28 sec |
| 4.8 | 2 min 20 sec | 1 min 21 sec |
| 5.0 | 2 min 0 sec | 3 min 00 sec |
| 5.3 | 3 min 0 sec | 2 min 20 sec |
| 5.5 | 1 min 0 sec | 1 min 20 sec |
| 5.8 | 1 min 10 sec | 1 min 30 sec |
| 6.0 | 1 min 10 sec | 1 min 40 sec |
| 6.3 | 1 min 0 sec | 1 min 46 sec |
| 6.5 | 0 min 50 sec | 1 min 30 sec |
| 6.8 | 0 min 50 sec | 1 min 10 sec |
| 7.0 | 0 min 20 sec | 0 min 58 sec |

The lyophilized daptomycin formulations of the presently disclosed subject matter were tested for daptomycin stability as a relative measure of daptomycin degradant impurity levels. The lyophilized daptomycin formulations were reconstituted in 0.9% sterile sodium chloride for injection the resultant solutions analysed by HPLC/UV. The amount of daptomycin and impurities in the solution were determined by % peak area at a wavelength of 223 nm. The total amount of impurities was calculated from the % peak area at a wavelength of 223 nm for all peaks other than that of daptomycin. The data are presented in the following Tables 4-9.

Table 4 displays the amount of total impurities, represented as % peak area, for each composition at 1, 2, 3 and 6 months after storage at 5, 25 and 40° C. The difference from the initial value is shown in parentheses.

TABLE 4

| Formulation at 5° C. | Total % Impurities Initial | Total % Impurities 1 month | Total % Impurities 2 months | Total % Impurities 3 months | Total % Impurities 6 months |
|---|---|---|---|---|---|
| A | 4.62 | Not tested | 4.82 (0.2) | 4.42 (−0.20) | Not tested |
| B | 4.64 | Not tested | Not tested | 4.88 (0.24) | Not tested |
| C | 4.97 | Not tested | Not tested | 4.60 (−0.37) | Not tested |
| D | 4.68 | Not tested | Not tested | 4.52 (−0.16) | Not tested |
| CUBICIN ® | 6.38 | Not tested | Not tested | 6.57 (0.19) | 6.89 (0.51) |

| Formulation at 25° C. | Total Impurities Initial | Total Impurities 1 month | Total Impurities 2 months | Total Impurities 3 months | Total Impurities 6 months |
|---|---|---|---|---|---|
| A | 4.62 | 4.98 (0.36) | 5.13 (0.51) | 4.42 (−0.2) | 5.28 (0.66) |
| B | 4.64 | 4.62 (−0.02) | 4.73 (0.09) | 5.13 (0.49) | Not tested |
| C | 4.97 | 4.59 (−0.38) | 4.75 (−0.22) | 5.13 (0.16) | Not tested |
| D | 4.68 | 4.45 (−0.23) | 4.60 (−0.08) | 4.91 (0.23) | Not tested |
| CUBICIN ® | 6.38 | 6.98 (0.60) | 6.71 (0.33) | 7.18 (0.80) | 7.87 (1.49) |

| Formulation at 40° C. | Total Impurities Initial | Total Impurities 1 month | Total Impurities 2 months | Total Impurities 3 months | Total Impurities 6 months |
|---|---|---|---|---|---|
| A | 4.62 | 4.68 (0.06) | Not tested | 5.83 (1.21) | Not tested |
| B | 4.64 | 5.29 (0.65) | 5.36 (0.72) | 5.77 (1.13) | Not tested |
| C | 4.97 | 5.98 (1.01) | 6.91 (1.94) | 7.79 (2.82) | Not tested |
| D | 4.68 | 4.97 (0.29) | 5.38 (0.70) | 5.89 (1.21) | Not tested |
| CUBICIN ® | 6.38 | Not tested | Not tested | Not tested | Not tested |

Table 5 displays the amount of the anhdyro daptomycin impurities, represented as % peak area, for each composition at 1, 2, 3 and 6 months after storage at 5, 25 and 40° C. The difference from the initial value is shown in parentheses.

TABLE 5

| | Anhydro Impurity Initial | Anhydro Impurity 1 month | Anhydro Impurity 2 months | Anhydro Impurity 3 months | Anhydro Impurity 6 months |
|---|---|---|---|---|---|
| Formulation at 5° C. | | | | | |
| A | 1.18 | Not tested | 1.1 (−0.08) | 1.06 (−0.12) | Not tested |
| B | 0.97 | Not tested | Not tested | 1.00 (0.03) | Not tested |
| C | 1.08 | Not tested | Not tested | 1.04 (−0.04) | Not tested |
| D | 1.11 | Not tested | Not tested | 1.09 (−0.02) | Not tested |
| CUBICIN ® | 1.71 | Not tested | Not tested | 1.69 (−0.02) | 2.06 (0.35) |
| Formulation at 25° C. | | | | | |
| A | 1.18 | 1.19 (0.01) | 1.29 (0.11) | 1.22 (0.04) | 1.45 (0.27) |
| B | 0.97 | 1.04 (0.07) | 1.11 (0.14) | 1.18 (0.21) | Not tested |
| C | 1.08 | 1.16 (0.08) | 1.27 (0.19) | 1.39 (0.31) | Not tested |
| D | 1.11 | 1.15 (0.04) | 1.16 (0.05) | 1.32 (0.21) | Not tested |
| CUBICIN ® | 1.71 | 1.92 (0.21) | 2.23 (0.52) | 2.06 (0.35) | 2.56 (0.85) |
| Formulation at 40° C. | | | | | |
| A | 1.18 | 1.48 (0.30) | Not tested | 1.72 (0.54) | Not tested |
| B | 0.97 | 1.33 (0.36) | 1.49 (0.52) | 1.63 (0.66) | Not tested |
| C | 1.08 | 1.71 (0.63) | 2.05 (0.97) | 2.49 (2.41)) | Not tested |
| D | 1.11 | 1.50 (0.39) | 1.71 (0.60) | 1.87 (0.76) | Not tested |
| CUBICIN ® | 1.71 | Not tested | Not tested | Not tested | Not tested |

Table 6 displays the amount of the hydrolysis daptomycin impurities, represented as % peak area, for each composition at 1, 2, 3 and 6 months after storage at 5, 25 and 40° C. The difference from the initial value is shown in parentheses.

TABLE 6

| | Hydrolysis Impurity Initial | Hydrolysis Impurity 1 month | Hydrolysis Impurity 2 months | Hydrolysis Impurity 3 months | Hydrolysis Impurity 6 months |
|---|---|---|---|---|---|
| Formulation at 5° C. | | | | | |
| A | 0.52 | Not tested | 0.57 (0.05) | 0.53 (0.01) | Not tested |
| B | 0.73 | Not tested | Not tested | 0.68 (−0.05) | Not tested |
| C | 0.62 | Not tested | Not tested | 0.53 (−0.09) | Not tested |
| D | 0.51 | Not tested | Not tested | 0.43 (−0.08) | Not tested |
| CUBICIN ® | 0.40 | Not tested | Not tested | 0.44 (0.04) | 0.45 (0.05) |
| Formulation at 25° C. | | | | | |
| A | 0.52 | 0.61 (0.09) | 0.64 (0.12) | 0.61 (0.09) | 0.62 (0.10) |
| B | 0.73 | 0.75 (0.02) | 0.79 (0.06) | 0.76 (0.03) | Not tested |
| C | 0.62 | 0.66 (0.04) | 0.71 (0.09) | 0.77 (0.15) | Not tested |
| D | 0.51 | 0.52 (0.01) | 0.55 (0.04) | 0.53 (0.02) | Not tested |
| CUBICIN ® | 0.40 | 0.49 (0.09) | 0.51 (0.11) | 0.56 (0.16) | 0.65 (0.25) |
| Formulation at 40° C. | | | | | |
| A | 0.52 | 0.66 (0.14) | Not tested | 0.86 (0.34) | Not tested |
| B | 0.73 | 0.89 (0.16) | 0.96 (0.23) | 1.02 (0.29) | Not tested |
| C | 0.62 | 0.98 (0.36) | 1.18 (0.56) | 1.39 (0.77) | Not tested |
| D | 0.51 | 0.64 (0.13) | 0.73 (0.22) | 0.80 (0.29) | Not tested |
| CUBICIN ® | 0.40 | Not tested | Not tested | Not tested | Not tested |

Table 7 displays the amount of the β-isomer daptomycin impurities, represented as % peak area, for each composition at 1, 2, 3 and 6 months after storage at 5, 25 and 40° C. The difference from the initial value is shown in parentheses.

TABLE 7

| | β-Isomer Impurity Initial | β-Isomer Impurity 1 month | β-Isomer Impurity 2 months | β-Isomer Impurity 3 months | β-Isomer Impurity 6 months |
|---|---|---|---|---|---|
| Formulation at 5° C. | | | | | |
| A | 0.56 | Not tested | 0.6 (0.04) | 0.62 (0.06) | Not tested |
| B | 0.64 | Not tested | Not tested | 0.70 (0.06) | Not tested |
| C | 0.62 | Not tested | Not tested | 0.63 (0.01) | Not tested |
| D | 0.57 | Not tested | Not tested | 0.60 (0.03) | Not tested |
| CUBICIN ® | 1.15 | Not tested | Not tested | 1.17 (0.02) | 1.17 (0.02) |
| Formulation at 25° C. | | | | | |
| A | 0.56 | 0.6 (0.04) | 0.6 (0.04) | 0.61 (0.05) | 0.64 (0.08) |
| B | 0.64 | 0.67 (0.03) | 0.67 (0.03) | 0.69 (0.05) | Not tested |
| C | 0.62 | 0.62 (0) | 0.62 (0.00) | 0.63 (0.01) | Not tested |
| D | 0.57 | 0.59 (0.02) | 0.59 (0.02) | 0.60 (0.03) | Not tested |
| CUBICIN ® | 1.15 | 1.16 (0.01) | 1.20 (0.05) | 1.17 (0.02) | 1.19 (0.04) |
| Formulation at 40° C. | | | | | |
| A | 0.56 | 0.54 (−0.02) | Not tested | 0.63 (0.07) | Not tested |
| B | 0.53 | Not tested | Not tested | Not tested | 0.59 (0.06) |
| C | 0.64 | 0.69 (0.05) | 0.68 (0.04) | 0.69 (0.05) | Not tested |
| D | 0.62 | 0.64 (0.02) | 0.64 (0.02) | 0.65 (0.03) | Not tested |
| E | 0.57 | 0.60 (0.03) | 0.61 (0.04) | 0.62 (0.05) | Not tested |
| CUBICIN ® | 1.15 | Not tested | Not tested | Not tested | Not tested |

The effect of pH on the stability of the lyophilized daptomycin formulations including citric acid were tested as a relative measure of daptomycin degradant impurity levels. The lyophilized daptomycin formulations, including 350 mg daptomycin, 56 mg citric acid, and sodium hydroxide sufficient to adjust the pH of the lyophilisation solution, were reconstituted in 0.9% sterile sodium chloride for injection and the resultant solutions analysed by HPLC/UV. Table 8 displays the amount of daptomycin impurities, represented as % peak area, for each composition upon initial preparation and after storage at 25° C. for 3 months. The difference from the initial value is shown in parentheses.

TABLE 8

| pH | Anhydro Impurities Initial | Anhydro Impurities 3 months | Hydrolysis Impurities Initial | Hydrolysis Impurities 3 months | β-Isomer Impurities Initial | β-Isomer Impurities 3 months |
|---|---|---|---|---|---|---|
| 2.5 | 0.83 | 1.10 (0.27) | 0.40 | 0.37 (−0.03) | 0.57 | 0.51 (−0.06) |
| 3.0 | 0.88 | 1.17 (0.29) | 0.45 | 0.42 (−0.03) | 0.58 | 0.52 (−0.06) |
| 3.3 | 0.88 | 1.19 (0.31) | 0.46 | 0.43 (−0.03) | 0.58 | 0.53 (−0.05) |
| 3.5 | 0.90 | 1.27 (0.37) | 0.47 | 0.46 (−0.01) | 0.58 | 0.54 (−0.04) |
| 3.8 | 0.93 | 1.32 (0.39) | 0.49 | 0.49 (0.00) | 0.59 | 0.54 (−0.05) |
| 4.0 | 0.93 | 1.25 (0.32) | 0.53 | 0.53 (0.00) | 0.60 | 0.56 (−0.04) |
| 4.3 | 0.94 | 1.26 (0.32) | 0.55 | 0.58 (0.03) | 0.61 | 0.58 (−0.03) |
| 4.5 | 0.96 | 1.27 (0.31) | 0.58 | 0.62 (0.04) | 0.62 | 0.58 (−0.04) |
| 4.8 | 0.95 | 1.26 (0.31) | 0.64 | 0.72 (0.08) | 0.65 | 0.61 (−0.04) |
| 5.0 | 0.95 | 1.23 (0.28) | 0.64 | 0.76 (0.12) | 0.65 | 0.62 (−0.03) |
| 5.3 | 0.90 | 1.15 (0.25) | 0.69 | 0.85 (0.16) | 0.66 | 0.63 (−0.03) |
| 5.5 | 0.87 | 1.10 (0.23) | 0.74 | 0.95 (0.21) | 0.68 | 0.65 (−0.03) |
| 5.8 | 0.83 | 1.01 (0.18) | 0.84 | 1.18 (0.34) | 0.72 | 0.67 (−0.05) |
| 6.0 | 0.80 | 0.94 (0.14) | 1.01 | 1.42 (0.41) | 0.74 | 0.69 (−0.05) |
| 6.3 | 0.74 | 0.89 (0.15) | 1.09 | 1.59 (0.50) | 0.76 | 0.72 (−0.04) |
| 6.5 | 0.69 | 0.86 (0.17) | 1.16 | 1.80 (0.64) | 0.77 | 0.76 (−0.01) |
| 6.8 | 0.65 | 0.80 (0.15) | 1.20 | 1.90 (0.70) | 0.77 | 0.74 (−0.03) |
| 7.0 | 0.64 | 0.78 (0.14) | 1.24 | 2.00 (0.76) | 0.79 | 0.83 (0.04) |

Table 9 displays the total amount of all daptomycin impurities, represented as % peak area, for each composition upon initial preparation and after storage at 25° C. for 3 months. The difference from the initial value is shown in parentheses.

TABLE 9

| pH | Total Impurities Initial | Total Impurities 3 months |
|---|---|---|
| 2.5 | 4.02 | 6.12 (2.10) |
| 3.0 | 4.18 | 5.68 (1.50) |
| 3.3 | 4.15 | 5.32 (1.17) |
| 3.5 | 4.21 | 5.37 (1.16) |

TABLE 9-continued

| pH | Total Impurities Initial | Total Impurities 3 months |
|---|---|---|
| 3.8 | 4.13 | 5.24 (1.11) |
| 4.0 | 4.32 | 5.16 (0.84) |
| 4.3 | 4.20 | 5.19 (0.99) |
| 4.5 | 4.31 | 5.21 (0.90) |
| 4.8 | 4.54 | 5.29 (0.75) |
| 5.0 | 4.36 | 5.34 (0.98) |
| 5.3 | 4.39 | 5.34 (0.95) |
| 5.5 | 4.57 | 5.45 (0.88) |
| 5.8 | 4.78 | 5.40 (0.62) |
| 6.0 | 4.74 | 5.57 (0.83) |
| 6.3 | 4.79 | 5.80 (1.01) |
| 6.5 | 4.97 | 6.60 (1.63) |
| 6.8 | 4.77 | 5.90 (1.13) |
| 7.0 | 4.84 | 6.19 (1.35) |

Example 2

The osmolalites of the presently disclosed lyophilized daptomycin formulations including citric acid (175 mM, 237.5 mM, 300 mM or 500 mM), ascorbic acid (237.5 mM or 300 mM) and 62.5 mg/mL daptomycin were assessed. Table 10 provides the osmolalities of the lyophilized daptomycin formulations including ascorbic acid, citric acid in either sterile water for injection ("WFI") or a 0.9% sodium chloride solution for injection. The pH of the reconstituted lyophilized daptomycin formulations was in the range of 4.45 to 4.74. The osmolalities of the CUBICIN® product and of a benchmark sucrose daptomycin formulation were included for comparison.

TABLE 10

| | | Osmolality (mOsmol/kg) | | | | | | | |
|---|---|---|---|---|---|---|---|---|---|
| | | Sucrose | | Citric acid | | | | Ascorbic acid | |
| | Infusion solution concentration | CUBICIN® CDF049M | 438 mM | 175 mM | 237.5 mM | 300 mM | 500 mM | 237.5 mM | 300 mM |
| NaCl reconstitution | IV Bolus (50 mg/mL) | 338 | 712 | 642 | 740 | 828 | 1156 | 636 | 705 |
| | IV Infusion (20 mg/mL) | 310 | 444 | 435 | 473 | 510 | 628 | 425 | 453 |
| | IV Infusion (10 mg/mL) | 302 | 36 | 364 | 383 | 400 | 464 | 357 | 367 |
| WFI reconstitution | IV Bolus (50 mg/mL) | 49 | 427 | Not tested | 458 | 572 | 940 | 343 | 421 |
| | IV Infusion (20 mg/mL) | 198 | Not tested | Not tested | Not tested | 398 | 562 | 315 | 344 |
| | IV Infusion (10 mg/mL) | 249 | 313 | Not tested | 327 | 344 | 422 | 306 | 321 |

The osmolalites of the ascorbic acid daptomycin formulations were lower than those of the citric acid daptomycin formulations.

Example 3

The reconstitution times, osmolalities, color appearances and stabilities of the presently disclosed lyophilized daptomycin formulations, e.g., including ascorbic acid, citric acid, and acetyl glucosamine as an additive and 62.5 mg/mL daptomycin, were assessed.

Reconstitution time was determined by injecting 7 mL of a 0.9% sodium chloride solution to a vial containing 350 mg/vial of lyophilized daptomycin. The resultant mixture was swirled for one minute and allowed to stand. The reconstitution time is the time required for addition of the diluent to total dissolution of the lyophilized daptomycin formulation.

TABLE 11

| Concentration of the additive | Average reconstitution time for a lyophilized daptomycin formulation including citric acid | Average reconstitution time for a lyophilized daptomycin formulation including ascorbic acid | Average reconstitution time for a lyophilized daptomycin formulation including acetyl glucosamine | Sucrose | CUBICIN® |
|---|---|---|---|---|---|
| 237.5 mM | 1 m 55 s (all samples, n = 15)[1] | 1 m 45 s (all samples) (n = 15) | 3 m 39 s (all samples, n = 15)[2] | 1 m 01 s (all samples) (n = 8) | 23 m 44 s (all samples) (n = 10) |

TABLE 11-continued

| Concentration of the additive | Average reconstitution time for a lyophilized daptomycin formulation including citric acid | Average reconstitution time for a lyophilized daptomycin formulation including ascorbic acid | Average reconstitution time for a lyophilized daptomycin formulation including acetyl glucosamine | Sucrose | CUBICIN® |
|---|---|---|---|---|---|
| 300 mM | 2 m 14 s (all samples, n = 30)[1] | 1 m 57 s (all samples, n = 30)[3] | 3 m 8 s (all samples, n = 30)[4] | | |

[1] 2 samples had a reconstitution time of >5 min
[2] 3 samples had a reconstitution time of >5 min
[3] 1 sample had a reconstitution time of >5 min
[4] 6 samples had a reconstitution time of >5 min Table 11 provides the average reconstitution times of the lyophilized daptomycin formulations including ascorbic acid, citric acid, and acetyl glucosamine in a 0.9% sodium chloride solution for injection. The pH of the reconstituted lyophilized daptomycin formulations was in the range of 4.45 to 4.74. The reconstitution times of the CUBICIN® product and of a benchmark sucrose daptomycin formulation were included for comparison.

Table 12 provides the osmolalities of the lyophilized daptomycin formulations including ascorbic acid, citric acid and acetyl glucosamine. These formulations were reconstituted with a 0.9% sterile sodium chloride solution for injection and WFI. The osmolalities of the CUBICIN® product and of a benchmark sucrose daptomycin formulation were included for comparison, as shown in Table 13.

TABLE 12

| Concentration of the additive | Administration | Osmolality of a lyophilized daptomycin formulation including citric acid | Osmolality of a lyophilized daptomycin formulation including ascorbic acid | Osmolality of a lyophilized daptomycin formulation including acetyl glucosamine |
|---|---|---|---|---|
| | | 0.9% Sodium Chloride reconstitution (mOsmol/Kg) | | |
| 237.5 mM | Bolus (50 mg/mL) | 740 | 636 | 548 |
| | Infusion (10 mg/mL) | 383 | 357 | 339 |
| | | WFI reconstitution (mOsmol/Kg) | | |
| | Bolus (50 mg/mL) | 458 | 343 | 249 |
| | Infusion (10 mg/mL) | 327 | 306 | 289 |
| | | 0.9% Sodium Chloride reconstitution (mOsmol/Kg) | | |
| 300 mM | Bolus (50 mg/mL) | 828 | 705 | 602 |
| | Infusion (10 mg/mL) | 400 | 367 | 346 |
| | | WFI reconstitution (mOsmol/Kg) | | |
| | Bolus (50 mg/mL) | 572 | 421 | 305 |
| | Infusion (10 mg/mL) | 344 | 321 | 297 |

TABLE 13

| Administration | Osmolality of Sucrose | Osmolality of CUBICIN® |
|---|---|---|
| 0.9% Sodium Chloride reconstitution (mOsmol/Kg) | | |
| Bolus (50 mg/mL) | 712 | 338 |
| Infusion (10 mg/mL) | 366 | 302 |
| WFI reconstitution (mOsmol/Kg) | | |
| Bolus (50 mg/mL) | 427 | 49 |
| Infusion (10 mg/mL) | 313 | 249 |

Table 14 provides the initial color appearances of the lyophilized daptomycin formulations including ascorbic acid, citric acid and acetyl glucosamine at a 50 mg/mL bolus or 10 mg/mL infusion solution exposed to a temperature of ambient laboratory temperature (about 20° C.) and a lighting condition of ambient laboratory lighting (about 400 lux). The color appearances of the CUBICIN® product and a benchmark sucrose daptomycin formulation were included for comparison.

TABLE 14

| Additive concentration | Citric acid | Ascorbic acid | Acetyl Glucosamine | Sucrose | CUBICIN® |
|---|---|---|---|---|---|
| 237.5 Mm 300 mM | Light yellow | Light yellow to light brown | Light yellow | Light yellow | Light yellow |

The lyophilized daptomycin formulations including ascorbic acid (237.5 mM and 300 mM), citric acid (237.5 mM and 300 mM), or acetyl glucosamine (237.5 mM and 300 mM), and 62.5 mg/mL daptomycin were tested for daptomycin stability as a relative measure of daptomycin degradant impurity level. The amount of daptomycin and impurities in the solution were determined by the % peak area at a wavelength of 223 nm. Table 15 displays the amount of daptomycin impurities, represented as % peak area, for each composition upon initial preparation and after storage at 25° C. and 40° C. for 2, 3 and 6 months. The difference from the initial value was shown in parentheses. The impurities of the CUBICIN® product and a benchmark sucrose daptomycin formulation were included for comparison.

TABLE 15

| Temperature (° C.) | Additive Concentration | Additive | Time point (month) | Impurity % Hydrolysis | Anhydro-Daptomycin | Impurity 1 | B isomer |
|---|---|---|---|---|---|---|---|
| 25° C. | 237.5 mM | Citric Acid | T = 0 | 0.43 | 1.05 | 0.12 | 0.57 |
| | | | T = 2 | 0.48 (0.06) | 1.02 (−0.03) | 0.07 (−0.05) | 0.57 (0.0) |
| | | | T = 3 | 0.46 (0.03) | 1.10 (0.05) | 0.07 (−0.05) | 0.52 (−0.05) |
| | | | T = 6 | 0.43 (0.00) | 1.11 (0.06) | 0.07 (−0.06) | 0.53 (−0.04) |
| | | Ascorbic Acid | T = 0 | 0.43 | 1.11 | 0.12 | 0.60 |
| | | | T = 2 | 0.52 (0.10) | 1.14 (0.03) | 0.14 (0.02) | 0.53 (−0.07) |
| | | | T = 3 | 0.52 (0.09) | 1.12 (0.01) | 0.12 (0.00) | 0.53 (−0.07) |
| | | | T = 6 | 0.46 (0.04) | 1.14 (0.03) | 0.29 (0.17) | 0.55 (−0.05) |
| | | Acetyl Glucosamine | T = 0 | 0.41 | 0.97 | 0.10 | 0.56 |
| | | | T = 2 | 0.45 (0.04) | 1.04 (0.07) | 0.07 (−0.03) | 0.52 (−0.04) |
| | | | T = 3 | 0.46 (0.05) | 1.10 (0.13) | 0.07 (−0.03) | 0.52 (−0.04) |
| | | | T = 6 | 0.43 (0.03) | 1.07 (0.10) | 0.12 (0.02) | 0.60 (0.04) |
| | 300 mM | Citric Acid | T = 0 | 0.40 | 1.05 | 0.12 | 0.56 |
| | | | T = 2 | 0.46 (0.06) | 1.03 (0.02) | 0.08 (−0.04) | 0.56 (0.00) |
| | | | T = 3 | 0.44 (0.04) | 1.13 (0.08) | 0.07 (−0.04) | 0.51 (−0.05) |
| | | | T = 6 | 0.40 (0.0) | 1.06 (0.01) | 0.06 (−0.05) | 0.51 (−0.05) |
| | | Ascorbic Acid | T = 0 | 0.42 | 1.13 | 0.11 | 0.59 |
| | | | T = 2 | 0.50 (0.08) | 1.16 (0.03) | 0.12 (0.02) | 0.53 (−0.06) |
| | | | T = 3 | 0.49 (0.07) | 1.12 (−0.01) | 0.11 (0.0) | 0.53 (−0.06) |
| | | | T = 6 | 0.45 (0.03) | 1.12 (−0.01) | 0.22 (0.12) | 0.54 (−0.05) |
| | | Acetyl Glucosamine | T = 0 | 0.40 | 0.97 | 0.10 | 0.59 |
| | | | T = 2 | 0.44 (0.04) | 1.03 (0.05) | 0.07 (−0.03) | 0.52 (−0.07) |
| | | | T = 3 | 0.44 (0.04) | 1.13 (0.16) | 0.07 (−0.03) | 0.51 (−0.07) |
| | | | T = 6 | 0.42 (0.02) | 1.05 (0.08) | 0.12 (0.02) | 0.59 (0.0) |
| | 438 mM | Sucrose (Benchmark formulation) | T = 0 | 0.53 | 0.91 | 0.08 | 0.53 |
| | | | T = 2 | 0.67 (0.14) | 0.99 (0.08) | 0.08 (0.0) | 0.59 (0.06) |
| | | | T = 3 | 0.58 (0.05) | 0.95 (0.04) | 0.06 (−0.02) | 0.52 (−0.01) |
| | | | T = 6 | 0.55 (0.02) | 0.98 (0.07) | 0.12 (0.04) | 0.48 (−0.05) |
| | | Cubicin ® | T = 0 | 0.79 | 2.38 | 0.28 | 1.13 |
| | | | T = 2 | 0.58 (−0.21) | 1.87 (−0.51) | 0.40 (0.12) | 1.15 (0.02) |
| | | | T = 3 | 0.60 (−0.19) | 1.94 (−0.44) | 0.19 (−0.09) | 1.08 (−0.05) |
| | | | T = 6 | 0.67 (−0.12) | 2.17 (−0.21) | 0.26 (−0.02) | 1.16 (0.03) |
| 40° C. | 237.5 mM | Citric Acid | T = 0 | 0.43 | 1.05 | 0.12 | 0.57 |
| | | | T = 1 | 0.48 (0.05) | 1.17 (0.12) | 0.08 (−0.05) | 0.55 (−0.03) |
| | | | T = 2 | 0.51 (0.09) | 1.26 (0.21) | 0.06 (−0.06) | 0.59 (0.01) |
| | | | T = 3 | 0.52 (0.09) | 1.27 (0.22) | 0.04 (−0.08) | 0.51 (−0.06) |
| | | | T = 6 | 0.57 (0.14) | 1.44 (0.39) | 0.12 (0.0) | 0.54 (−0.03) |
| | | Ascorbic Acid | T = 0 | 0.43 | 1.11 | 0.12 | 0.60 |
| | | | T = 1 | 0.59 (0.16) | 1.25 (0.14) | 0.19 (0.07) | 0.61 (0.01) |
| | | | T = 2 | 0.63 (0.21) | 1.30 (0.20) | 0.31 (0.19) | 0.63 (−0.03) |
| | | | T = 3 | 0.66 (0.23) | 1.32 (0.22) | 0.22 (0.10) | 0.57 (−0.03) |
| | | | T = 6 | 0.66 (0.23) | 1.40 (0.29) | 0.27 (0.15) | 0.71 (0.11) |
| | | Acetyl Glucosamine | T = 0 | 0.41 | 0.97 | 0.10 | 0.56 |
| | | | T = 1 | 0.47 (0.06) | 1.13 (0.16) | 0.08 (−0.02) | 0.54 (−0.02) |
| | | | T = 2 | 0.49 (0.09) | 1.20 (0.23) | 0.09 (−0.01) | 0.64 (0.08) |
| | | | T = 3 | 0.50 (0.09) | 1.26 (0.29) | 0.04 (−0.06) | 0.56 (0.0) |
| | | | T = 6 | 0.54 (0.13) | 1.52 (0.55) | 0.26 (0.16) | 0.71 (0.15) |
| | 300 mM | Citric Acid | T = 0 | 0.40 | 1.05 | 0.12 | 0.56 |
| | | | T = 1 | 0.44 (0.04) | 1.19 (0.13) | 0.08 (−0.05) | 0.54 (−0.02) |
| | | | T = 2 | 0.47 (0.07) | 1.28 (0.23) | 0.06 (−0.06) | 0.55 (−0.02) |
| | | | T = 3 | 0.48 (0.08) | 1.25 (0.20) | 0.05 (−0.07) | 0.50 (−0.06) |
| | | | T = 6 | 0.50 (0.10) | 1.40 (0.35) | 0.14 (0.02) | 0.55 (−0.01) |
| | | Ascorbic Acid | T = 0 | 0.42 | 1.13 | 0.11 | 0.59 |
| | | | T = 1 | 0.55 (0.13) | 1.24 (0.11) | 0.16 (0.06) | 0.60 (0.01) |
| | | | T = 2 | 0.60 (0.18) | 1.28 (0.15) | 0.25 (0.14) | 0.62 (0.03) |
| | | | T = 3 | 0.59 (0.17) | 1.29 (0.16) | 0.18 (0.07) | 0.56 (−0.03) |
| | | | T = 6 | 0.60 (0.18) | 1.32 (0.19) | 0.26 (0.15) | 0.69 (0.10) |
| | | Acetyl Glucosamine | T = 0 | 0.40 | 0.97 | 0.10 | 0.59 |
| | | | T = 1 | 0.46 (0.06) | 1.11 (0.14) | 0.08 (−0.02) | 0.54 (−0.05) |
| | | | T = 2 | 0.48 (0.08) | 1.16 (0.19) | 0.09 (−0.01) | 0.60 (0.01) |
| | | | T = 3 | 0.47 (0.07) | 1.19 (0.22) | 0.09 (−0.01) | 0.55 (−0.04) |
| | | | T = 6 | 0.57 (0.17) | 1.40 (0.43) | 0.11 (0.01) | 0.65 (0.06) |

TABLE 15-continued

| Temperature (° C.) | Additive Concentration | Additive | Time point (month) | Impurity % | | | |
|---|---|---|---|---|---|---|---|
| | | | | Hydrolysis | Anhydro-Daptomycin | Impurity 1 | B isomer |
| | 438 mM | Sucrose (Benchmark formulation) | T = 0 | 0.53 | 0.91 | 0.08 | 0.53 |
| | | | T = 1 | 0.59 (0.06) | 1.05 (0.14) | 0.06 (−0.02) | 0.64 (0.31) |
| | | | T = 2 | 0.67 (0.14) | 1.13 (0.22) | 0.06 (−0.02) | 0.58 (0.05) |
| | | | T = 3 | 0.59 (0.06) | 1.11 (0.20) | 0.15 (0.07) | 0.53 (0.0) |
| | | | T = 6 | 0.55 (0.02) | 1.24 (0.33) | 0.14 (0.06) | 0.48 (−0.05) |
| | | Cubicin ® | T = 0 | 0.51 | 1.55 | 0.30 | 1.14 |
| | | | T = 1 | 0.79 (0.28) | 2.38 (0.83) | 0.28 (−0.02) | 1.13 (−0.01) |
| | | | T = 2 | 0.94 (0.43) | 2.80 (1.25) | 0.29 (−0.02) | 1.16 (0.02) |
| | | | T = 3 | 1.04 (0.53) | 3.20 (1.65) | 0.22 (0.07) | 1.10 (−0.04) |
| | | | T = 6 | 1.24 (0.73) | 3.70 (2.15) | N/A | 1.20 (0.06) |

As shown in Table 15, when stored at 25° C. for 6 months, the anhydro daptomycin impurities increased up to about 0.1% for all formulations compared to the initial value, which was comparable to the benchmark Sucrose daptomycin formulation. Impurity 1 increased by about 0.2% for both 237.5 mM and 300 mM lyophilised ascorbic acid daptomycin formulations, by about 0.02% for both 237.5 mM and 300 mM lyophilised acetyl glucosamine daptomycin formulations, while remained stable for both 237.5 mM and 300 mM lyophilised citric acid daptomycin formulations, which was comparable to benchmark Sucrose daptomycin formulation and the CUBICIN® product. All other major impurities remained stable without significant increases. The β-isomer daptomycin impurity remained stable for almost all formulations.

When stored at 40° C. for 6 months, differences in the increases of anhydro daptomycin impurities were observed between citric acid formulations and ascorbic acid formulations. Impurity 1 & β-isomer daptomycin impurities remained stable for the citric acid formulations, however increased up to 0.2% & 0.1%, respectively, for the ascorbic acid formulations, compared to the initial value. Hydrolysis impurity increased up to 0.14% for the citric acid formulations (0.14% for the 237.5 mM formulation, and 0.1% for the 300 mM formulation). Hydrolysis impurity increased up to 0.23% for the ascorbic acid formulations (0.23% for the 237.5 mM formulation, and 0.18% for the 300 mM formulation). Hydrolysis impurity increased up to 0.17% for the acetyl glucosamine formulations (0.14% for the 237.5 mM formulation, and 0.17% for the 300 mM formulation). Anhydro daptomycin impurities increased up to 0.39% for the citric acid formulations and up to 0.29% for the ascorbic acid formulations, which was comparable to the Sucrose formulation. The rate of increase for anhydro daptomycin impurities was the lowest for the 300 mM ascorbic acid formulation. The rates of increase for all other major impurities were approximately double for ascorbic acid formulations compared to citric acid formulations.

The above-presented stability data showed that citric acid lyophilized daptomycin formulations have a slight advantage over ascorbic acid lyophilized daptomycin formulations and acetyl glucosamine lyophilized daptomycin formulations as citric acid lyophilized daptomycin formulations would tolerate heat excursions better than ascorbic acid lyophilized daptomycin formulations and acetyl glucosamine lyophilized daptomycin formulations.

The impurity amounts or stability for the 237.5 mM formulations were comparable to the 300 mM formulations, e.g., the 237.5 mM formulation was not significantly different from the 300 mM formulation for citric acid. In some examples, a 237.5 mM formulation concentration is preferred at least because it has lower osmolality, and it is possibly easy to register lower the amounts of the additives.

Example 4

The color appearances of the presently disclosed lyophilized daptomycin formulations, e.g., including ascorbic acid (237.5 mM and 300 mM) or citric acid (237.5 mM and 300 mM) and 62.5 mg/mL daptomycin at 50 mg/mL IV bolus or 10 mg/mL IV infusion at initial, 4, 24, and 48 hours exposed to room temperature and lighting conditions of about 400 lux, were assessed. The color appearances for the CUBICIN® product and for a benchmark sucrose daptomycin formulation were included for comparison. The lyophilized daptomycin formulations and the benchmark sucrose daptomycin formulation were reconstituted in both 0.9% NaCl and WFI.

In a 50 mg/mL IV bolus solution, the general color trend of all daptomycin formulations was a light yellow at initial and four hours followed by an increase in color intensity to yellow at 24 to 48 hours. The benchmark sucrose daptomycin formulation was a slightly dull/less intense yellow. Both 237.5 mM and 300 mM citric acid daptomycin formulations were equivalent to the CUBICIN® product in color. Both 237.5 mM and 300 mM ascorbic acid daptomycin formulations were slightly more intense yellow in color than the CUBICIN® product at 24 to 48 hours.

10 mg/mL IV infusion solution, the general color trend of all solutions was light yellow, which remained light yellow over time to 48 hours. The benchmark sucrose daptomycin formulation was slightly less intense yellow. Both 237.5 mM and 300 mM citric acid daptomycin formulations were equivalent to the CUBICIN® product in color. Both 237.5 mM and 300 mM ascorbic acid daptomycin formulations were slightly lighter then the CUBICIN® product at 24 to 48 hours.

Therefore, all reconstituted solutions were essentially yellow with any variation considered different shades of yellow compared to the yellow of the CUBICIN® product. The color differences between the ascorbic acid daptomycin formulations and the CUBICIN® product were subtle. Therefore, the reconstituted solution color of both citric acid and ascorbic acid daptomycin formulations are acceptable.

The presently disclosed subject matter is not to be limited in scope by the specific embodiments described herein. Indeed, various modifications of the presently disclosed subject matter in addition to those described herein will become apparent to those skilled in the art from the foregoing description. Such modifications are intended to fall within the scope of the appended claims.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of the application.

All publications, patents and patent applications cited herein are hereby expressly incorporated by reference for all purposes to the same extent as if each was so individually denoted.

What is claimed is:

1. A lyophilized daptomycin formulation comprising a lyophilizate of an aqueous solution of daptomycin and an additive selected from the group consisting of pharmaceutically acceptable organic acids and pharmaceutically acceptable salts thereof, acetyl glucosamine, and combinations thereof, wherein the pharmaceutically acceptable organic acids and pharmaceutically acceptable salts thereof, if present, have a concentration of from 10 mM to 500 mM in the aqueous solution prior to lyophilization.

2. The lyophilized daptomycin formulation of claim 1, wherein the formulation comprises from about 200 mg to about 600 mg of daptomycin.

3. The lyophilized daptomycin formulation of claim 1, wherein the pharmaceutically acceptable organic acid is selected from the group consisting of monocarboxylic organic acids, dicarboxylic organic acids, hydroxyl substituted dicarboxylic organic acids, tricarboxylic organic acids, hydroxyl substituted tricarboxylic organic acids, tetracarboxylic organic acids, and combinations thereof.

4. The lyophilized daptomycin formulation of claim 3, wherein the pharmaceutically acceptable organic acid is a hydroxyl substituted tricarboxylic organic acid.

5. The lyophilized daptomycin formulation of claim 4, wherein the hydroxyl substituted tricarboxylic organic acid is citric acid.

6. A reconstituted daptomycin formulation comprising the lyophilized daptomycin formulation of claim 1, wherein the lyophilized formulation is reconstituted in a pharmaceutically acceptable diluent to obtain the reconstituted daptomycin formulation.

7. The reconstituted daptomycin formulation of claim 6, wherein the lyophilized formulation is reconstituted in the pharmaceutically acceptable diluent in less than about 5 minutes.

8. The reconstituted daptomycin formulation of claim 6, wherein the concentration of daptomycin in the reconstituted daptomycin formulation is from about 20 mg/mL to about 100 mg/mL.

9. The reconstituted daptomycin formulation of claim 6, wherein the concentration of the additive in the reconstituted daptomycin formulation is from about 1 mM to about 500 mM.

10. The reconstituted daptomycin formulation of claim 9, wherein the concentration of the additive in the reconstituted daptomycin formulation is about 237.5 mM.

11. The reconstituted daptomycin formulation of claim 9, wherein the concentration of the additive in the reconstituted daptomycin formulation is about 300 mM.

12. The reconstituted daptomycin formulation of claim 6, wherein the concentration of the additive in the reconstituted daptomycin formulation is from about 1 mg/mL to about 500 mg/mL.

13. The reconstituted daptomycin formulation of claim 6, wherein the pH of the reconstituted daptomycin formulation is from about 4.0 to about 5.0.

14. The reconstituted daptomycin formulation of claim 13, wherein the pH of the reconstituted daptomycin formulation is about 4.7.

15. The reconstituted daptomycin formulation of claim 6, wherein the diluent is selected from the group consisting of sterile water for injection, bacteriostatic water for injection, 0.45% sodium chloride solution for injection, 0.9% sodium chloride solution for injection, Ringer's solution, lactated Ringer's solution, and combinations thereof.

16. The reconstituted daptomycin formulation of claim 15, wherein the diluent is 0.9% sterile sodium chloride solution for injection.

17. The reconstituted daptomycin formulation of claim 15, wherein the diluent is sterile water for injection.

18. A method of treating a bacterial infection in a subject, comprising administering to the subject an effective amount of a reconstituted daptomycin formulation of claim 6.

19. A method of treating a biofilm, the method comprising exposing a surface of a device to a solution comprising an effective amount of a reconstituted daptomycin formulation of claim 6.

20. A method for preparing a lyophilized daptomycin formulation of claim 1, wherein the method comprises:
(a) forming an aqueous solution of daptomycin and an additive, which is selected from the group consisting of pharmaceutically acceptable organic acids and pharmaceutically acceptable salts thereof, acetyl glucosamine, and combinations thereof, wherein the pharmaceutically acceptable organic acids and pharmaceutically acceptable salts thereof, if present, have a concentration of from 10 mM to 500 mM in the aqueous solution;
(b) adjusting the pH to from about 4.0 to about 5.0; and
(c) lyophilizing the solution to obtain a lyophilizate.

21. A method for preparing a lyophilized daptomycin formulation of claim 1, wherein the method comprises:
(a) forming an aqueous solution of daptomycin at a pH of from about 4.0 to 5.0;
(b) dissolving an additive selected from the group consisting of pharmaceutically acceptable organic acids, pharmaceutically acceptable salts thereof and acetyl glucosamine in the aqueous solution of the daptomycin, wherein the pharmaceutically acceptable organic acids and pharmaceutically acceptable salts thereof, if present, have a concentration of from 10 mM to 500 mM in the aqueous solution;
(c) adjusting the pH to from about 4.0 to about 5.0; and
(d) lyophilising lyophilizing the solution to obtain a powder.

* * * * *